(12) United States Patent
Durkee

(10) Patent No.: US 6,957,582 B1
(45) Date of Patent: Oct. 25, 2005

(54) ULTRASONIC SYSTEM AND METHOD OF GAUGING AIRCRAFT FUEL AND DETECTING BATTLE DAMAGE

(75) Inventor: Scott Robert Durkee, New Haven, VT (US)

(73) Assignee: Simmonds Precision Products, Inc., Vergennes, VT (US)

( * ) Notice: Subject to any disclaimer, the term of this patent is extended or adjusted under 35 U.S.C. 154(b) by 0 days.

(21) Appl. No.: 10/878,034

(22) Filed: Jun. 28, 2004

(51) Int. Cl.[7] .......................... G01N 29/04; G01F 23/28
(52) U.S. Cl. ........................ 73/602; 73/614; 73/290 V; 310/319
(58) Field of Search .......................... 73/627–632, 583, 73/52, 597, 598, 599, 600, 644, 290 V, 290 R, 73/602, 614; 310/319, 334; 367/141, 152

(56) References Cited

U.S. PATENT DOCUMENTS

| | | | |
|---|---|---|---|
| 4,320,659 A | * | 3/1982 | Lynnworth et al. ........... 73/589 |
| 4,774,842 A | * | 10/1988 | Kollar et al. ................. 73/640 |
| 5,185,579 A | * | 2/1993 | Mertens et al. ............. 324/527 |
| 6,236,142 B1 | | 5/2001 | Durkee |
| 6,443,012 B2 | * | 9/2002 | Beardmore ................... 73/626 |
| 6,536,275 B1 | | 3/2003 | Durkee et al. |

* cited by examiner

Primary Examiner—Helen Kwok
(74) Attorney, Agent, or Firm—Peter M. Hernandez, Esq.; Calfee, Halter & Griswold LLP

(57) ABSTRACT

An aircraft ultrasonic system for fuel gauging and battle damage detection comprises: at least one ultrasonic transducer disposed at a fuel tank of the aircraft; a first circuit for exciting the at least one ultrasonic transducer to transmit an acoustic pulse toward a surface of fuel in the tank, the at least one ultrasonic transducer operative to receive acoustic echo pulses reflected from the fuel surface and convert the acoustic echo pulses to electrical echo pulses, the at least one ultrasonic transducer also operative to receive acoustic compression wavefront pulses impinging thereon and convert the acoustic compression wavefront pulses to electrical compression wavefront pulses; and a second circuit for receiving and processing the electrical echo and compression wavefront pulses from the at least one ultrasonic transducer, the second circuit operative to perform fuel quantity measurements using the electrical echo pulses and to perform battle damage detection using the electrical compression wavefront pulses. A counterpart method is further disclosed.

20 Claims, 3 Drawing Sheets

ULTRASONIC SYSTEM AND METHOD OF GAUGING AIRCRAFT FUEL AND DETECTING BATTLE DAMAGE

BACKGROUND OF THE INVENTION

The present invention relates generally to ultrasonic fuel gauging systems, and more particularly, to an aircraft ultrasonic fuel gauging system adapted to also assess battle damage to the aircraft and a counterpart method of performing the same.

Generally, aircraft ultrasonic fuel gauging systems include one or more ultrasonic transducers disposed at a fuel tank of the aircraft for determining the quantity of fuel in the tank. The transducers are excited periodically to transmit pulses directed toward the surface of the fuel in the tank and receive echoes which are processed to determine the level of fuel in the tank based on time of flight and other calculations. An exemplary ultrasonic fuel gauging system is disclosed in the U.S. Pat. No. 6,236,142 B1, granted to Durkee et al. on May 22, 2001, entitled "Ultrasonic Fuel Gauging System" and assigned to the same assignee as the instant application, which patent being incorporated by reference herein.

Battle damage to an aircraft, caused, for example, by projectiles penetrating the airframe or fuel tank itself, has been determined heretofore by a separate and independent system which adds volume and weight to the aircraft. Aircraft designers prefer to keep the weight of the avionics to a minimum to save on the amount of fuel to complete a mission. Moreover, since the aircraft has a limited volume for storage of avionics, it is desirable to reduce the size of or eliminate avionics wherever possible.

Accordingly, it is desirable to combine the functions of fuel gauging and battle damage assessment in a common avionics instrument, if possible. The present invention provides for a common avionics system which satisfies this desire.

SUMMARY OF THE INVENTION

In accordance with one aspect of the present invention, an aircraft ultrasonic system for fuel gauging and battle damage detection comprises: at least one ultrasonic transducer disposed at a fuel tank of the aircraft; a first circuit for exciting the at least one ultrasonic transducer to transmit an acoustic pulse toward a surface of fuel in the tank, the at least one ultrasonic transducer operative to receive acoustic echo pulses reflected from the fuel surface and convert the acoustic echo pulses to electrical echo pulses, the at least one ultrasonic transducer also operative to receive acoustic compression wavefront pulses impinging thereon and convert the acoustic compression wavefront pulses to electrical compression wavefront pulses; and a second circuit for receiving and processing the electrical echo and compression wavefront pulses from the at least one ultrasonic transducer, the second circuit operative to perform fuel quantity measurements using the electrical echo pulses and to perform battle damage detection using the electrical compression wavefront pulses.

In accordance with another aspect of the present invention, a method of processing ultrasonic pulses for gauging fuel and detecting battle damage of an aircraft comprises the steps of: disposing at least one ultrasonic transducer at a fuel tank of the aircraft; exciting the at least one ultrasonic transducer to transmit an acoustic pulse toward a surface of fuel in the tank; receiving both acoustic echo pulses reflected from the fuel surface and acoustic compression wavefront pulses conducted through the fuel by the at least one ultrasonic transducer and generating electrical pulses representative thereof; and processing said electrical echo and compression wavefront pulses to perform fuel quantity measurements using the electrical echo pulses and battle damage detection using the electrical compression wavefront pulses.

DETAILED DESCRIPTION OF THE INVENTION

Figure 1:
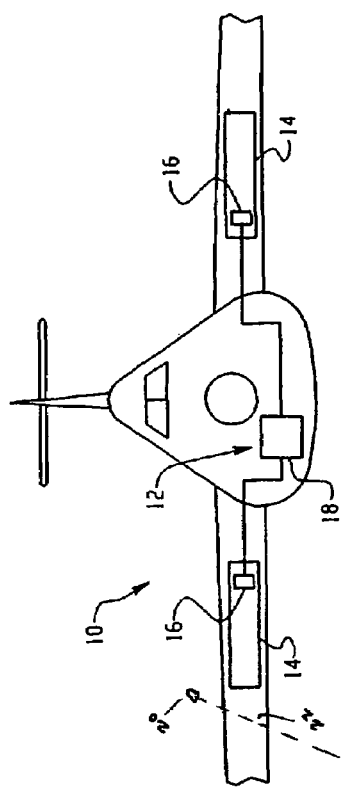
FIG. 1 is an exemplary aircraft suitable for accommodating an embodiment of the present invention.

Referring to FIG. 1, an aircraft 10, which may be a manned or unmanned vehicle, for example, is shown including an ultrasonic processing system 12 which performs both fuel quantity measurement and battle damage assessment. The aircraft 10 includes a fuel system comprising one or more fuel tanks 14 containing aircraft fuel for operating the aircraft through its mission. For example, the aircraft 10 may have a tank 14 supported by the airframe in each of its wings as illustrated in FIG. 1. However, it is understood that the fuel tanks may be disposed at other points on the aircraft just as well without deviating from the principles of the present invention. Located in each tank 14 is at least one ultrasonic transducer, collectively designated as block 16 in FIG. 1, which provides ultrasonic information to a processor unit 18 through transmitting and receiving circuits. In accordance with the present invention, should the aircraft incur battle damage during its mission, like from a projectile 20 striking the airframe at point 22, for example, the processing unit 18 will, in addition to determining fuel quantity of tank 14, assess risk of such damage from the ultrasonic signal provided to it by the ultrasonic transducer(s) 16 at the tank 14 as will become more evident from the description infra.

Figure 2:
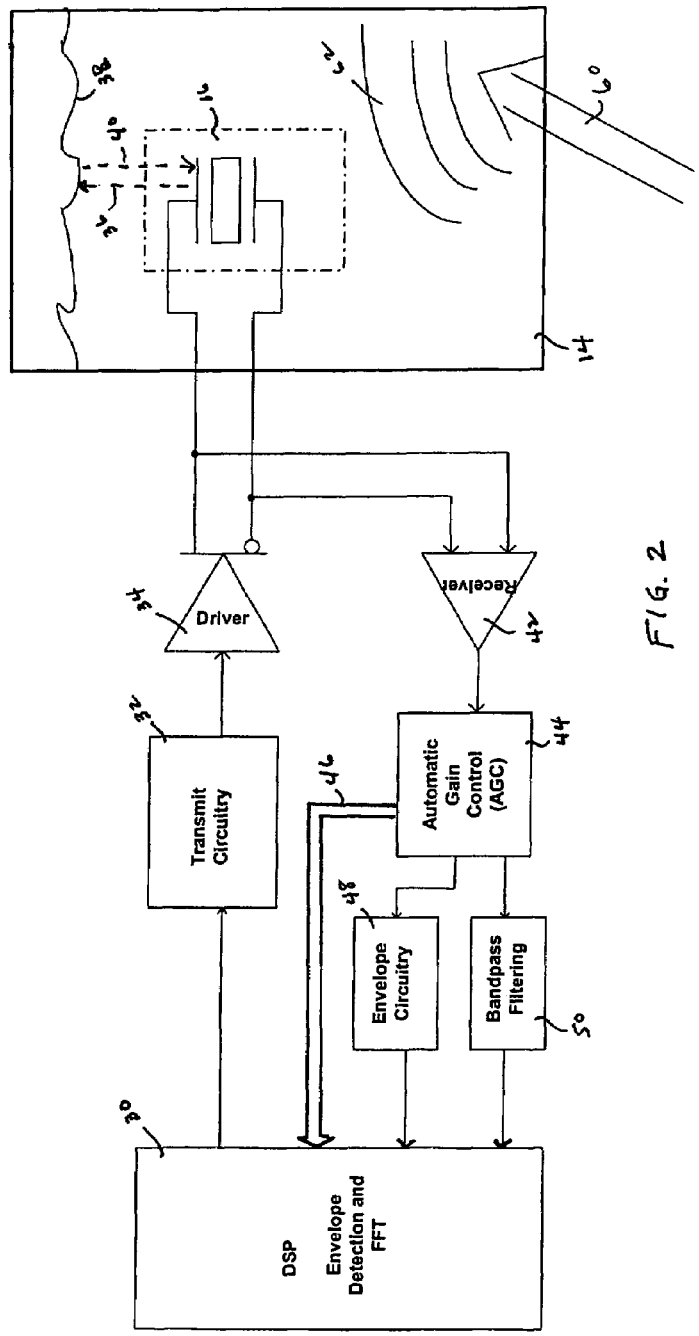
FIG. 2 is a block diagram schematic of an ultrasonic system suitable for embodying an aspect of the present invention.

A block diagram schematic of an ultrasonic processing system 12 suitable for embodying the principles of the present invention is shown in FIG. 2. Referring to FIG. 2, a programmed processor 30, which may be a digital signal processor (DSP), like a Texas Instruments TMS320, for example, governs the operations of the transmitting and receiving circuits and performs the calculations and analysis of the received pulses from the at least one ultrasonic transducer 16 in each fuel tank 14. The ultrasonic transducer 16 of the present embodiment is an active piezo resonator transducer high Q tuned at approximately one (1) megahertz (MHz) for optimal sensitivity in the longitudinal mode.

During a battle damage event, like a high energy projectile striking the aircraft structure, for example, large shear mode waves are created and conducted along the structure to the fuel tank. At the fuel tank, the shear mode waves are converted to the form of compressional waves that may be conducted through the fuel of the tank and detected by the transducer 16. If a high energy projectile strikes the aircraft fuel tank itself, compressional waves will emanate from the point of projectile contact through the fuel and be detected by the transducer 16.

In order to achieve functionality as both a fuel gauging sensor and a battle damage detector, the transducer 16 may be isolated from the aircraft structure in the longitudinal mode which may be accomplished by providing a significant acoustic impedance Z mismatch between the aircraft structure and the active piezo sensor, preferably for both the longitudinal and radial modes of the transducer even though the fuel will only support compressional (longitudinal) waves. To maintain high electromechanical efficiency, the transducer 16 should be prevented from converting the usable longitudinal mode energy into radial modes which may occur if sufficient acoustic impedance matching occurs on the radial circumference of the transducer.

Generally, ultrasonic fuel gauging transducers do respond to other frequency bands in the longitudinal mode, but to a reduced sensitivity due to the λ/4 matching layer's dependence on the high Q tuned frequency. Such sub-resonance bands may include 550 kHz, 600 kHz and 900 kHz, for example. Since sufficient energy does exist in these sub-resonance bands during battle damage events, the transducer 16 is quite useful in detecting the compression waves introduced into the fuel from such events. The duration and magnitude of transducer excitation may be indicative of a compression wave event in the fuel. In addition, since the piezo-resonator transducer is highly dependent upon the direction of an incoming compression wavefront, the frequency content of the compression wave may be a distinguishing feature in a signal processing algorithm for use in assessing a detected compression wave for risk of a battle damage event and for alerting the operator and/or autocontrol system of the aircraft of such risk.

Thus, the ultrasonic transducer 16 of the present embodiment may perform dual duty as both a fuel quantity measurement sensor and an aircraft structure battle damage detector. The ultrasonic transducer 16 is preferably disposed at the bottom of the tank 14 and in one embodiment, may be embedded in a composite structure of the tank with a transducer window for transmission and reception of pulses in contact with the fuel. A suitable ultrasonic transducer embodiment for use in the present embodiment is exemplified in the U.S. Pat. No. 6,536,275 B1, issued to Durkee et al. on Mar. 25, 2003, entitled "Ultrasonic Transducer For Liquid Measurement" and assigned to the same assignee as the instant application, which patent being incorporated by reference herein.

Referring to FIG. 2, transmit circuitry 32 may be coupled to and governed by the processor 30 to electrically excite the transducer 16 via a driver circuit 34. The processor 30 may include data input and sampling and digitizing circuits for reading in signals for processing digitally. For fuel quantity measurement purposes, the transmit circuitry 32 may be governed to electrically excite the transducer 16 periodically with an approximately one megahertz pulse of a duration of 1–4 microseconds every 200 milliseconds or so or about 5 times a second. While in the present embodiment, the processor 30 governs the transmit circuit 32 to excite the transducer 16, it is understood that the transmit circuit 32 may operate just as well autonomously to excite the transducer 16 without deviating from the principles of the present invention.

The output of the driver circuit 34 may be coupled to a receiver circuit 42 for detecting the initial time of excitation which is passed to the processor 30 through an automatic gain control (AGC) circuit 44 and signal lines 46 which will be described in greater detail below. The transducer 16 converts the electrical excitation pulse into an acoustic pulse which is directed over a path 36 toward the surface 38 of the fuel where it is reflected back to the transducer 16 over a path 40. The transducer 16 receives the surface reflected pulse and reconverts it to an electrical pulse which is conducted to the receiver circuit 42.

The receiver circuit 42 is operative to condition the reflected pulses and conduct them to the AGC circuit 44. When the AGC circuit 44 detects a pulse of sufficient amplitude, it alerts the processor 30 of the presence of the pulse and provides the gain associated therewith over signal lines 46. The processor 30 is thus made aware that a pulse has been received and the amplitude range thereof from the signals 46. The purpose of the AGC circuit 44 is to keep the received pulse within the amplitude range of downstream envelope and bandpass filter circuits 48 and 50, respectively. In the present embodiment, the receiver 42 is designed to accommodate pulses which may range in amplitude over orders of magnitude. However, the amplitude range of the circuits 48 and 50 are limited. Therefore, the AGC circuit 44 detects the amplitude range of the received pulse and adjusts the gain thereof to render the amplitude within the range of the circuits 48 and 50. The resultant gain of the AGC circuit 44 for each pulse is provided to the processor 30 over signal lines 46 so that it may readjust the amplitude of the signal received from circuits 48 and 50 to their proper settings.

The AGC circuit 44 provides the amplitude range adjusted signal to both the envelope circuit 48 and bandpass filter circuit 50. The envelope circuit 48 forms an envelope pulse from the peak amplitudes of the frequency content of the received pulse. The formed envelope pulse is conducted from the circuit 48 to the processor 30. Likewise, the filter circuit 50 bandpass filters the output pulse signal from the AGC 44 so that the pulse provided to the processor 30 is restricted to only relevant frequency content. In the present embodiment, the bandpass filter may pass frequencies in the range from say 100 kHz to 2 MHz, for example, which will include the tuned resonance frequency of the transducer and the sub-resonance frequencies thereof.

Accordingly, transmitted and reflected envelope pulses of the transducer 16 are conducted from the circuit 48 to the processor 30 which performs certain well-known time-of-flight and other calculations to determine the quantity of fuel in the tank 14. The processor 30 may ascertain transmitted pulses from the driver circuit 34 and reflected echo pulses from the transducer 16 from the amplitude, duration and frequency content thereof. Generally, transmitted pulses are approximately 20 volts in amplitude, 1–4 microseconds in duration and approximately 1 MHz in frequency. Similarly, reflected pulses may range from 15 millivolts to 2 volts and from 4 to 20 microseconds in duration and are approximately 1 MHz in frequency.

When a projectile impacts the airframe at or near the fuel tank 14 as shown by the arrowed double line 60, compression waves are created in the fuel of the tank 14 and impinges upon and excites the transducer 16. Since the fuel only supports compression waves and not shear waves, the transducer 16 may not respond to any shear wave component created in the aircraft structure as a result of the impact event. Due to the broadband nature of the compression wave, the transducer 16 may be excited not only at its tuned resonance frequency, but also at its sub-resonance frequencies as well. Pulsed electrical excitation signals produced by the transducer 16 in response to the compression wave excitation are conducted to the receiver circuit 42 and AGC circuit 44 which responds by alerting the processor 30 of the received pulse and the gain associated with the amplitude thereof via signal lines 46. The gain adjusted pulse is conducted to the circuits 48 and 50. An envelope of the gain adjusted pulse produced by the circuit 48 and a filtered pulse signal produced by the circuit 50 are conducted to the processor 30 for further processing therein to assess risk of battle damage to the aircraft. The signature of a compression wave pulse is readily distinguishable from a transmitted or echo pulse as will be better understood from the following description.

Figure 3:
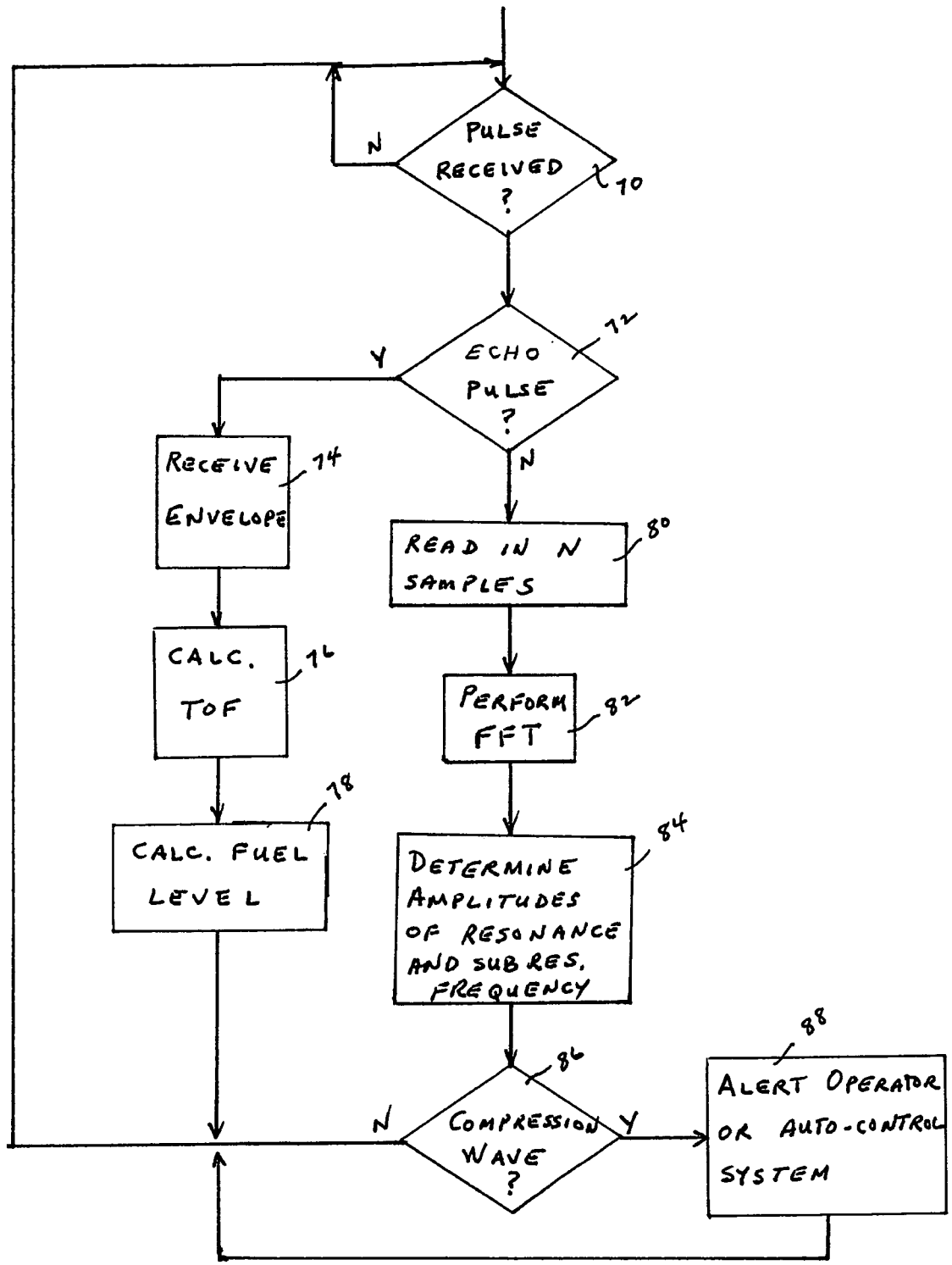
FIG. 3 is a flowchart of an exemplary algorithm suitable for use in the embodiment of FIG. 2.

A suitable algorithm for use by the processor 30 for operating on the received and conditioned pulses to distinguish between echo and compression wave pulses and perform the tasks associated with each is shown by the flowchart of FIG. 3. Referring to FIG. 3, the flowchart may start with decisional block 70 wherein the processor 30 may wait to receive an indication from the AGC 44 via signal lines 46 that a pulse has been received. The task processing of the processor 30 may be interrupted by a pulse reception signal or the processor 30 may poll the signal lines 46 periodically to determine pulse reception. In any event, when a pulse is received, it is determined in decisional block 72 if the pulse is a transmitted or echo pulse for use in fuel quantity measurements or a compression wave pulse for use in determining risk of aircraft battle damage.

This may be accomplished using a number of discriminates. For example, transmission pulses may be identified by their time of occurrence and amplitude which is generally known apriori. In addition, if the pulse is received outside of an echo reception time window which is usually set to last for a period of approximately two milliseconds from a transmission, it is considered a compression wave pulse. If the pulse is received within the set reception window, then the amplitude and duration of the envelope pulse of circuit 48 is used to identify an echo pulse. As noted above, echo pulses are quite small in amplitude compared with the compression pulses created by a projectile impact event.

If the pulse is determined to be an echo pulse, then processing is directed to block 74 wherein the envelope echo pulse is analyzed to determine if it came from the fuel surface or from another interface. If the pulse resulted from the fuel surface interface, then a time-of-flight (TOF) calculation is performed in block 76 which is used in a fuel level calculation in block 78. Fuel quantity nay be determined from the fuel level measurement using additional knowledge of the fuel and dimensions of the tank through well-known calculations. Thereafter, processing may be returned to block 70 to wait for another pulse.

If the pulse is determined not to be a transmitted or echo pulse by block 72, then processing continues at block 80 wherein N samples of the pulse are read into the processor 30 from circuit 50 utilizing the sampling and digitizing circuits thereof. The N samples may be processed in block 82 by a fast Fourier transform (FFT), for example, to determine the frequency content thereof. The number of time samples N is determined by the size of the FFT. For example, if the FFT is a 16 point FFT, i.e. producing a spectrum of 16 discrete frequency bins, then 16 time samples are used, and so on. In the next block 84, the amplitudes of the FFT produced frequency bins are determined and from this information, it is determined in block 86 if the compression wave contains sufficient energy to be indicative of a risk of battle damage to the aircraft.

For example, FFT produced frequencies at the excitation sub-resonances of the transducer 16 may be analyzed for content. If the content of these sub-resonant frequencies are above a predetermined level, then it is likely that the compression wave pulse is indicative of battle damage. In addition, the time duration of the incoming pressure wave created by a projectile impact may often greatly exceed the normal fuel surface echo pulse duration and thus, may be also used as a discriminator for battle damage detection or the risk thereof.

Once it is determined that there is risk of battle damage to the aircraft from block 86, then if the aircraft is a manned aircraft, the operator may be alerted through a visual and/or audible alert by block 88 so that the operator may confirm the assessment through other parameters. If the aircraft is a UAV, then a signal may be sent to the auto-controller by block 88 for assessment confirmation through pre-established logic. In any event, a decision may be made by either the operator or auto-controller as to whether or not to continue the flight and complete the mission, attempt to return to base or take other appropriate measures.

Figure 4:
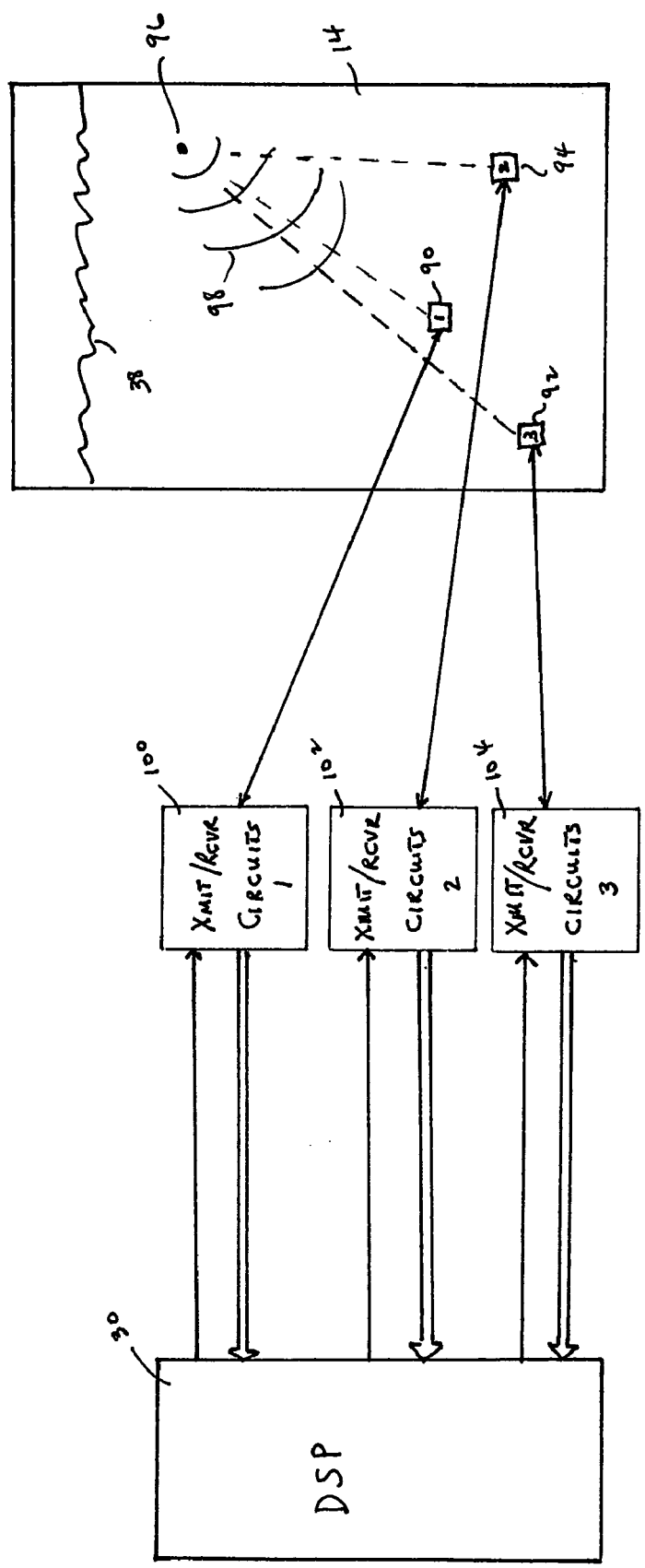
FIG. 4 is a block diagram illustration of an ultrasonic system suitable for embodying another aspect of the present invention.

If a plurality of ultrasonic transducers 90, 92 and 94 are disposed at known locations of the tank 14 as shown in the illustration of FIG. 4, then a location 96 of a projectile impact may be established by determining the relative direction of the resulting compression wavefront 98 from the measurements of the plurality of transducers. In the embodiment of FIG. 4, each transducer 90, 92 and 94 is coupled through transmit/receive circuits 100, 102 and 104, respectively, to the processor 30. Each circuit 100, 102 and 104 may be the same as or similar to the circuitry described in connection with the embodiment of FIG. 2 in structure and operation. Thus, as electrical pulses are produced by the transducers 90, 92 and 94, they will be received and conditioned respectively by the circuits 100, 102 and 104 and processed by the processor 30 in a similar manner to that described in connection with the flowchart of FIG. 3. Thus, the electrical pulses produced by the transducers 90, 92 and 94 as a result of excitation by the compression wave 98 will be processed by the processor 30 to establish the location of the impact source 96.

This may be done by comparing the times of arrival of the electrical pulses produced by the transducers 90, 92 and 94 as a result of excitation by the compression wave 98. For example, assuming the impact occurred at a single point source and since the location of the transducers 90, 92, and 94 are known, the relative time of arrival of the impact compression wave at each transducer may be used in a triangulation algorithm to estimate the point of actual impact.

While the present invention has been described herein above in connection with one or more embodiments, it is understood that such description was presented solely by way of example. Accordingly, the present invention should not be limited to any of the presented embodiments, but rather construed in breadth and broad scope in accordance with the recitation of the claims appended hereto.

What is claimed is:

1. An aircraft ultrasonic system for fuel gauging and battle damage detection of an aircraft, said system comprising:

at least one ultrasonic transducer disposed at a fuel tank of the aircraft;

a first circuit for exciting said at least one ultrasonic transducer to transmit an acoustic pulse toward a surface of fuel in said tank, said at least one ultrasonic transducer operative to receive acoustic echo pulses reflected from the fuel surface and convert said acoustic echo pulses to electrical echo pulses, said at least one ultrasonic transducer also operative to receive acoustic compression wavefront pulses impinging thereon and convert said acoustic compression wavefront pulses to electrical compression wavefront pulses; and a second circuit for receiving and processing said electrical echo and compression wavefront pulses from said at least one ultrasonic transducer, said second circuit operative to perform fuel quantity measurements using said electrical echo pulses and to perform battle damage detection using said electrical compression wavefront pulses.

2. The system of claim 1 wherein the second circuit is operative to identify said received compression wavefront pulses and said received echo pulses.

3. The system of claim 2 wherein the second circuit is operative to determine that a received pulse is not an echo pulse based on a time of reception thereof in relation to the transmission pulse.

4. The system of claim 3 wherein the second circuit is operative to determine that a received pulse is not an echo pulse if the reception thereof falls outside a predetermined time window from the transmission pulse.

5. The system of claim 4 wherein the second circuit is operative to distinguish echo pulses falling within the predetermined time window from compression wavefront pulses falling within the predetermined time window based on pulse amplitudes thereof.

6. The system of claim 2 wherein the second circuit is operative to analyze an identified compression wavefront pulse based on frequency content thereof for performing battle damage detection.

7. The system of claim 6 wherein the second circuit is operative to perform a frequency transformation of compression wavefront pulses to determine the frequency content thereof.

8. The system of claim 7 wherein the second circuit includes a digital processing system operative to sample, digitize and frequency transform time samples of the compression wavefront pulses to determine the frequency content thereof.

9. The system of claim 7 wherein the second circuit is operative to detect battle damage based on the magnitude of the frequency content of the compression wavefront pulses.

10. The system of claim 1 including at least three ultrasonic transducers for detecting acoustic echo pulses and acoustic compression wavefront pulses and generating electrical echo and compression wavefront pulses in response thereto; and wherein the second circuit is operative to determine the location of a source of compression wavefront pulse generation based on the electrical compression wavefront pulses generated from said at least three ultrasonic transducers.

11. Method of processing ultrasonic pulses for gauging fuel and detecting battle damage of an aircraft, said method comprising the steps of:

disposing at least one ultrasonic transducer at a fuel tank of the aircraft;

exciting said at least one ultrasonic transducer to transmit an acoustic pulse toward a surface of fuel in said tank;

receiving both acoustic echo pulses reflected from the fuel surface and acoustic compression wavefront pulses conducted through the fuel by said at least one ultrasonic transducer and generating electrical echo and compression wavefront pulses representative thereof; and processing said electrical echo and compression wavefront pulses to perform fuel quantity measurements using said electrical echo pulses and battle damage detection using said electrical compression wavefront pulses.

12. The method of claim 11 including the step of identifying electrical compression wavefront pulses and electrical echo pulses.

13. The method of claim 12 wherein the step of identifying includes determining that a received pulse is not an echo pulse based on a time of reception thereof in relation to the transmission pulse.

14. The method of claim 12 wherein the step of identifying includes determining that a received pulse is not an echo pulse if a reception thereof falls outside a predetermined time window from the transmission pulse.

15. The method of claim 14 including the step of distinguishing echo pulses falling within the predetermined time window from compression wavefront pulses falling within the predetermined time window based on pulse amplitudes thereof.

16. The method of claim 12 including the step of analyzing an identified compression wavefront pulse based on frequency content thereof for performing battle damage detection.

17. The method of claim 16 wherein the step of analyzing includes performing a frequency transformation of compression wavefront pulses to determine the frequency content thereof.

18. The method of claim 16 wherein the step of analyzing includes frequency transforming time samples of the compression wavefront pulses to determine the frequency content thereof.

19. The method of claim 16 including the step of detecting battle damage based on the magnitude of the frequency content of the compression wavefront pulses.

20. The method of claim 11 including the steps of: disposing at least three ultrasonic transducers at the fuel tank of the aircraft for detecting acoustic echo pulses and acoustic compression wavefront pulses and generating electrical echo and compression wavefront pulses in response thereto; and determining the location of a source of compression wavefront pulse generation based on the electrical compression wavefront pulses generated from said at least three ultrasonic transducers.

* * * * *